United States Patent [19]

Abegg et al.

[11] 3,958,581

[45] May 25, 1976

[54] COSMETIC COMPOSITION CONTAINING A CATIONIC POLYMER AND DIVALENT METAL SALT FOR STRENGTHENING THE HAIR

[75] Inventors: Jean-Louis Abegg; Jean-Pierre Boiteux, both of Paris; Colette Hourseau, Herblay, all of France

[73] Assignee: L'Oreal, Paris, France

[22] Filed: Oct. 15, 1974

[21] Appl. No.: 515,074

Related U.S. Application Data

[63] Continuation-in-part of Ser. No. 361,329, May 17, 1973, abandoned.

[30] Foreign Application Priority Data

May 17, 1972 Luxemburg............................ 65373

[52] U.S. Cl................................. 132/7; 252/DIG. 2; 252/DIG. 3; 252/DIG. 13; 424/DIG. 1; 424/DIG. 2; 424/47; 424/70; 424/71; 424/78; 424/80; 424/81
[51] Int. Cl.² ....................... A45D 7/04; A45D 7/06
[58] Field of Search................... 424/47, 70, DIG. 1, 424/DIG. 2, 71; 132/7

[56] References Cited

UNITED STATES PATENTS

| | | | |
|---|---|---|---|
| 3,186,911 | 6/1965 | Rieger et al. | 424/71 |
| 3,208,910 | 9/1965 | Cassidy | 424/70 |
| 3,472,243 | 10/1969 | Wall et al. | 132/7 |
| 3,530,215 | 9/1970 | Grief et al. | 424/70 |
| 3,715,428 | 2/1973 | Quasius et al. | 424/47 |
| 3,849,548 | 11/1974 | Grand | 424/70 |
| 3,850,178 | 11/1974 | Schoenholz | 132/7 |
| 3,876,760 | 4/1975 | Nersesian et al. | 424/70 |

*Primary Examiner*—Sam Rosen
*Assistant Examiner*—Vera C. Clarke
*Attorney, Agent, or Firm*—Cushman, Darby & Cushman

[57] ABSTRACT

A cosmetic composition to strengthen the hair which comprises (a) a cosmetic vehicle containing a member selected from water, ethanol, isopropanol or mixtures thereof (b) 0.2 to 25 percent by weight of a cationic polymer and (c) 0.01 – 0.5 mole per gram of cationic polymer of a divalent metal salt selected from the carbonate, silicate, nitrate, acetate, gluconate, pantothenate and lactate of calcium, magnesium, manganese, iron, strontium, zinc and cadmium.

11 Claims, No Drawings

COSMETIC COMPOSITION CONTAINING A CATIONIC POLYMER AND DIVALENT METAL SALT FOR STRENGTHENING THE HAIR

This application is a continuation-in-part of our application Ser. No. 361,329, filed May 17, 1973, now abandoned.

The present invention relates to new cosmetic compositions for strengthening the hair, particularly degraded hair, as well as to a process for treating hair with said compositions.

It is well known, for instance, that different chemical treatments, applied to the hair, have the effect of weakening the mechanical or physical properties of the keratin of the hair and thus render the hair fragile and brittle.

Representative of such chemical treatments is a permanent waving operation whereby deformation of the hair occurs by initially opening the S—S linkages of the keratin with the aid of a reducing compound such as thioglycolic acid, ammonium thioglycolate, thioglycerol or thiolactic acid, and then by reconstituting these keratinic linkages with the aid of an oxidizing agent which, for the most part, is either hydrogen peroxide or a persalt.

Other known chemical operations which weaken the keratin of the hair include bleaching treatments which, in certain cases, can be very damaging, these bleaching operations being usually accomplished with the aid of a peroxide. Further, the dyeing of hair, especially when it is repeated at regular intervals also has the effect of degrading the hair, and thus renders it very weak and brittle.

Besides these conventional chemical treatments, the hair also suffers some degradation, more or less severe, from the action of certain atmospheric agents such as the sun, and more particularly, sea water.

To render the thus degraded hair more vigorous and lively and thereby improve its general appearance, there has been proposed heretofore a variety of treatments utilizing a variety of compositions.

Specifically it has been proposed to treat degraded hair with protein-based compositions and more particularly protein hydrolyzate based compositions. To the same end, it has also been proposed to use compositions containing certain cationic polymers.

These different types of known compositions have effectively imparted certain beneficial properties to the keratin of the hair and in particular have provided good protection against subsequent treatments utilizing chemical agents, such as those conventionally employed in permanent hair waving operations, as well as bleaching and dyeing operations.

After extensive research, the applicants have found in a quite surprising way that the use, in the treatment of the hair and, particularly degraded hair, of certain cosmetic compositions containing, in combination, at least one cationic polymer and at least one non-toxic salt of a divalent metal, provides results far superior to those achieved with known compositions. Thus, the compositions of the present invention provide improved protection for the hair against subsequent conventional chemical treatment and it imparts to the hair not only excellent mechanical stability but also improved mechanical resistance when the hair is subjected to an elongation of 15% (Index $I_{15}$) - a property of great importance in capillary cosmetology.

Thus the present invention relates to new cosmetic compositions for treating hair, particularly degraded hair, so as to strengthen its mechanical stability, these compositions being characterized by the fact that they are homogeneous and contain in an appropriate cosmetic vehicle at least one cationic polymer carrying at least one and preferably several tertiary amine groups or quaternary ammonium groups, and at least one non-toxic salt of a divalent metal soluble in water or in 50/50 hydroalcoholic solutions.

Hair which has been treated with the composition of the present invention not only exhibits excellent mechanical stability but is also soft to the touch, has good liveliness and a most shiny appearance. Further, the hair wave achieved after treatment with a hair waving formulation containing the composition of this invention has excellent holding power and the hair is supple and exhibits beautiful waves.

The cationic polymers usefully employed in the compositions of the present invention belong to a class of well known compounds. In a general fashion this term "cationic polymers" means those polymers exhibiting in their principal chain or in the substituted form, at least one tertiary amine or quaternary ammonium group. Usually the cationic polymers employed in the compositions of the present invention have an average molecular weight between about 1000 and 3,000,000.

Representative cationic polymers which can be used in accordance with the present invention include, especially, the following polymers:

1. The quaternary derivatives of cellulose ether of the formula

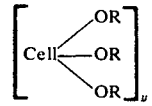

wherein Cell represents the residue of an anhydroglucose unit, $y$ represents a whole number between about 50 and about 20,000, and preferably between about 200 and about 5000, and the radicals R, identical or different, represent a group of the formula

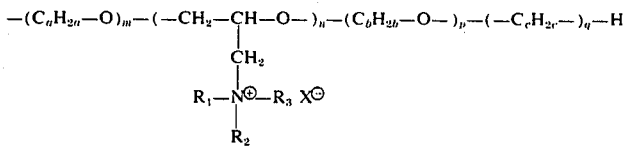

wherein $a$ and $b$ are 2 or 3; $c$ is 1, 2 or 3; $m$ and $p$ are whole numbers from 0 to 10; $n$ is a whole number from 0–3; $q$ is 0 or 1; $R_1$, $R_2$ and $R_3$ each independently represent alkyl, aryl, aralkyl, alkaryl, alkoxyalkyl or alkoxyaryl, containing 1–10 carbon atoms and such that the sum of the number of carbon atoms of $R_1$, $R_2$ and $R_3$ varies from 3–12; it being understood that when any one of $R_1$, $R_2$ and $R_3$ is alkoxy alkyl, there are at least two carbon atoms between the oxygen of the alkoxy moiety and the nitrogen atom to which the alkyl moiety is attached; and $X^-$ represents the anionic residue of a mineral or organic acid.

Representative anoins designated as $X^\ominus$, include, for instance, chloride, bromide, iodide, sulfate, bisulfate ($HSO_4^-$), $CH_3SO_3^-$, sulfonate, phosphate, acetate and the like.

The average value of $n$ is between about 0.01 and 1 per anhydroglucose unit, and preferably between about 0.1 and 0.5.

The average value of $(m+n+p+q)$ is between about 0.01 – 4 per unit of anhydroglucose.

Such quaternary derivatives of cellulose ether are described, for instance, in French Patent 1,492,597 as well as in U.S. Pat. No. 3,472,840 incorporated herein by reference.

The quaternary derivatives of cellulose ether can be prepared in accordance with processes described in these two patents, for instance, by etherification and quaternization; these two operations being able to be made in any order or even simultaneously.

The etherification operation effects the fixation on the cellulose chain of a short chain alkyl or hydroxy alkyl substituent having, for example, up to 4 carbon atoms, and preferably an alkyl substituent having 1–3 carbon atoms or a hydroxyalkyl substituent having from 2–4 carbon atoms.

To effect etherification there is employed, preferably, an alkylating agent such as dimethylsulfate, diethyl sulfate, methyl chloride, methyl bromide, ethyl chloride, ethyl bromide or n-propyl chloride; or a hydroxy alkylating agent such as ethylene oxide or propylene oxide.

For the quaternization reaction, there is employed a quaternary halohydrin of the formula:

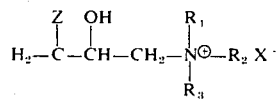

or a quaternary epoxide of the formula

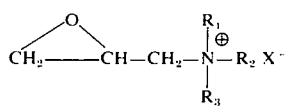

wherein $R_1$, $R_2$ and $R_3$ are defined above, Z is Cl, I or Br, and $X^-$ is an anion and preferably the anion residue of a strong mineral acid.

The radicals R fixed on the anhydroglucose chain can be, for example, the following: H, $-CH_3$, $-C_2H_5$, $-CH_2CH_2OH$, $-(CH_2CH_2O)_s-CH_2OH$ wherein $s$ is 1 or 2,

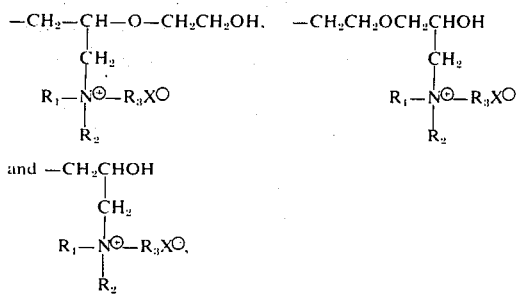

wherein $R_1$, $R_2$ and $R_3$ are defined as above and represent for example methyl or ethyl, with X being, for example, Cl.

Representative quaternary derivatives of cellulose ether include, for example, the polymer formed by the reaction of hydroxyethylcellulose (having a degree of substitution of hydroxyethyl groups of 1.3) with the reaction product of 0.7 mole of epichlorohydrin and 0.7 mole of trimethylamine per unit of substituted anhydroglucose, the resulting polymer having an average molecular weight of 200,000 to 230,000.

The degree of substitution of the groups with the quaternary nitrogen must be such that the molecular weight of the substituted hydroxyethylcellulose polymer varies between 2000 and about 3,000,000.

When the quaternized polymer of cellulose ether is prepared starting with a cellulose ether, the later is preferably selected from the group consisting of non-ionic water soluble cellulose ethers and non-ionic water soluble cellulose ethers substituted by a short chain alkyl or hydroxyalkyl. These derivatives are, principally methyl-, ethyl-, or hydroxyethyl-cellulose.

Representative quaternized derivatives of cellulose ethers usefully employed in the present invention include the commercial product JR-IL or JR-400 sold by Union Carbide.

2. Copolymers of the formula

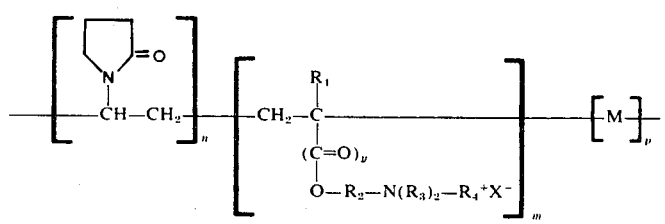

wherein, on the basis of 100 moles of monomer units (i.e. $m+n+p = 100$) $n$ is a whole number between 20 and 99, $m$ is a whole number between 1 and 80 and $p$ is a whole number between 0 and 50; $y = 0$ or 1; $R_1$ represents hydrogen or methyl; $R_2$ represents

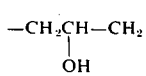

or $C_xH_{2x}$ wherein $x$ is a whole number between 2 and 18; $R_3$ is methyl, ethyl or tert-butyl; $R_4$ is methyl, ethyl or benzyl; $X^-$ represents a chloride, bromide, iodide, sulfate, bisulfate or $CH_3SO_3^-$ anion; and M represents a copolymerizable vinyl monomer unit.

The optionally present copolymerizable vinyl monomer representdd by M in the foregoing formula, is a conventional vinyl monomer copolymerizable with N-vinyl pyrrolidone. These vinyl monomers are principally alkyl vinyl ethers wherein the alkyl moiety has preferably from 1–8 carbon atoms, for example, methyl vinyl ether, ethyl vinyl ether, octyl vinyl ether; alkyl esters of acrylic or methacrylic acid, principally those wherein the alkyl moiety has from 1–4 carbon atoms, for instance, methyl acrylate or methyl methacrylate; vinyl aromatic monomers such as styrene and α-methyl styrene; vinyl esters such as vinyl acetate; vinylidene chloride; acrylonitrile; methacrylonitrile; acrylamide; methacrylamide; vinyl chloride; and alkyl crotonates, wherein the alkyl moiety has, preferably, from 1 to 8 carbon atoms and the like.

These copolymers are prepared by copolymerization of (1) N-vinylpyrrolidone, (2) the acrylate or methacrylate of di-lower alkyl-amino alkyl or the acrylate or methacrylate of di-lower alkyl amino hydroxyalkyl; and (3) optionally another vinyl monomer copolymerizable with the vinylpyrrolidone. Taking 100% as the molar basis, the units of vinylpyrrolidone represent from 20–99%, the units attributable to the acrylate or methacrylate represent between 1 and 80% and the units attributable to the other copolymerizable vinyl monomer represent between 0 and 50%.

Representative acrylates or methacrylates usefully employed in the production of such copolymers are principally the following:
dimethylaminomethyl acrylate,
dimethylaminomethyl methacrylate,
diethylaminomethyl acrylate,
diethylaminomethyl methacrylate,
dimethylaminoethyl acrylate,
dimethylaminoethyl methacrylate,
dimethylamino-2-hydroxypropyl acrylate,
dimethylamino-2-hydroxypropyl methacrylate,
diethylamino-2-hydroxyethyl acrylate,
diethylamino-2-hydroxyethyl methacrylate,
dimethylaminobutyl acrylate,
dimethylaminobutyl methacrylate,
dimethylaminoamyl methacrylate,
diethylaminoamyl methacrylate,
dimethylaminohexyl acrylate,
diethylaminohexyl methacrylate,
dimethylaminooctyl acrylate,
dimethylaminooctyl methacrylate and
diethylaminooctyl acrylate.

The molecular weight of these copolymers is generally between 15,000 and 1,000,000 and more particularly between 50,000 and 500,000.

Representative of such copolymers are copolymers known under the commercial name of GAFQUAT 734 and 755, sold by GAF. The average molecular weight of GAFQUAT 734 is about 100,000 and that of GAFQUAT 755 is greater than 1,000,000.

Such polymers are described in French Patent No. 71 03017, in the name of GAF Corporation, incorporated herein by reference.

3. Copolymers of the general formula

- A - Z - A - Z - A - Z - wherein A represents a radical containing two secondary amine functions, preferably a radical derived from a heterocycle containing two secondary amine functions, e.g. the radical

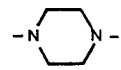

and

Z represents a divalent radical B or B' wherein B and B', identical or different, represent a straight or branched chain alkylene having up to 6 carbon atoms in the principal chain and also be able to carry oxygen, nitrogen and/or sulfur atoms and from 1–3 aromatic or heterocyclic rings the oxygen, nitrogen and sulfur atoms can be present in the form of ether, thioether, sulfoxide, sulfone, sulfonium, amine, amine oxide, quaternary ammonium, amide, imide, urea, alcohol, ester and/or urethane groups.

These copolymers can be quaternized by lower alkyl or lower alkyl phenyl groups, principally, methyl, ethyl or benzyl groups.

The quaternization can be effected, for instance, with the aid of known quaternization agents such as, for example, lower alkyl chloride, bromide, iodide, sulfate, mesylate or tosylate or benzyl chloride or bromide.

These copolymers have an average molecular weight generally between 1000 and 15,000.

Representative of these copolymers are, in particular, those obtained by the polycondensation of piperazine and epichlorohydrin. The molar proportion of piperazine to epichlorohydrin can vary, for instance, from 0.5:2 to 2:0.5. These polycondensates can also be quaternized by lower alkyl or lower alkyl phenyl radicals as indicated above.

Such copolymers are described in Luxembourg patent 64371 as well as in its corresponding U.S. patent application Ser. No. 310,088, filed Nov. 28, 1972, now U.S. Pat. No. 3,917,817, incorporated herein by reference.

4. The polymers of etherified starch of the formula

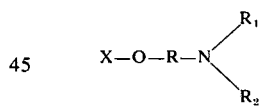

wherein X represents the residue of a starch molecule, R is alkylene or hydroxyalkylene, wherein the alkylene contains from 2 to 5 carbon atoms and $R_1$ and $R_2$ are alkyl containing 1 to 5 carbon atoms, aryl, or aralkyl where the aryl moiety can be phenyl and the alkyl moiety can contain from 1 to 5 carbon atoms.

The polymers are described in U.S. Pat. Nos. 2,813,093 and 3,186,911, incorporated herein by reference.

The starch can be, for example, corn starch, wheat starch or potato starch. Preferably, the starch employed is one which contains from 25–50% by weight of amylose and 50–75% by weight of amylopectin. This starch is etherified by the group,

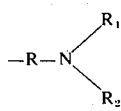

The proportion of hydroxyl groups of starch which are etherified is such that the cationic polymer contains preferably from about 0.25 – 2% by weight of nitrogen, as determined by the Kjeldahl method. Such polymers are described in U.S. Pat. Nos. 2,813,093 and 3,186,911.

5. The copolymers resulting from the copolymerization of 43–16 weight percent methyl methacrylate, 54–25 weight percent dimethylaminoethyl methacrylate and 12–52 weight percent octadecyl methacrylate.

These copolymers can be used either in the form of the free base, or in the quaternized form, or even in the crosslinked form. These copolymers generally have a molecular weight between 10,000 and 1,500,000.

Such copolymers are described in French Patent No. 72 32244, or in its corresponding U.S. patent application Ser. No. 287,845 filed Sept. 11, 1972, incorporated herein by reference.

As indicated above, these copolymers can be cross-linked with a cross-linking agent possessing two unsaturated groups, for example, with the aid of diethylene glycol methacrylate.

The amount of cross-linking agent is generally less than 0.15 weight percent.

The copolymers can also be quaternized with the aid of an alkylating or an aralkylating agent such as for, example, dimethyl sulfate, lower alkyl halides such as methyl iodide or ethyl bromide, 2-bromo-ethanol or benzyl halide.

In accordance with the present invention, the concentration of the cationic polymer is generally between about 0.2 and 25 weight percent, preferably between about 0.5 and 12 weight percent, based on the total weight of the composition.

As has been stated previously, the cosmetic compositions according to the invention contain, in addition to the cationic copolymer, at least one non-toxic salt of a divalent metal, soluble in water or in a 50/50 hydroalcoholic solution, wherein the alcohol is generally a lower alkanol. In this context, the term "metal" includes the alkaline earth metals.

Representative non-toxic salts of divalent metals usefully employed in the present invention include the carbonates, silicates, nitrates, acetates, gluconates, pantothenates and lactates of calcium, magnesium, manganese, iron, strontium, zinc and cadmium.

The concentration of these salts of a divalent metal in the compositions of the present invention is generally between about 0.005 – 0.05 mole/gram of cationic polymer and, preferably, about 0.01 mole/gram of cationic polymer.

The different comparative tests that have been carried out have shown that the presence of at least one salt of a divalent metal is indispensible in the attainment of the highly desirable results that have been achieved by the present invention, to wit: a remarkable strenghtening of the mechanical stability of degraded hair, although the exact mechanism of the action of these salts of divalent metals has not yet been fully understood.

In accordance with the present invention, the cosmetic compositions can be provided in a variety of forms and, in particular, in the form of an aqueous, alcoholic or hydroalcoholic solution wherein the alcohol employed can be an aliphatic alcohol such as ethyl alcohol or isopropyl alcohol. Alternatively the cosmetic compositions can be provided in the form of an aerosol spray or foam.

The pH of the compositions of the present invention is generally between about 3–9 and preferably between about 6–8.

According to one particular embodiment of the present invention the compositions comprise an aqueous, alcoholic or hydroalcoholic solution and are usefully employed as a hair waving lotion. In this embodiment, the concentration of the cationic polymer is generally between 1 and 3% with the non-toxic salt of said divalent metal being present therein in the amounts previously specified.

In addition to the cationic polymer and the non-toxic salt of a divalent metal, the composition can, in this embodiment, also contain other cosmetic resins in amounts ranging between about 0.2 and 1 weight percent. Representative of such cosmetic resins are polyvinylpyrrolidone, having a molecular weight between 10,000 and 70,000; copolymers of vinylpyrrolidone/vinyl acetate, 70:30% to 30:70% (K in 1% ethanol = 25–50); copolymers of vinyl acetate and an unsaturated carboxylic acid such as crotonic acid (90:10) having a molecular weight of about 20,000; copolymers resulting from the copolymerization of vinyl acetate (75–85%), crotonic acid (5–15%) and an acrylic or methacrylic ester (5–15%) or an alkyl vinyl ether (5–15%) having a molecular weight of about 50,000; copolymers resulting from the copolymerization of vinyl acetate (63–88%), crotonic acid (5–15%) and (a) a vinyl ester of a long carbon chain acid of 10–22 carbon atoms or (b) an allyl or methallyl ester of a long carbon chain acid of 10–22 carbon atoms having a molecular weight of about 50,000; copolymers resulting from the copolymerization of (a) an ester of an unsaturated alcohol having 2–12 carbon atoms and short carbon chain saturated carboxylic acid having 2–5 carbon atoms (65–80%), (b) of an unsaturated short carbon chain acid having 4–12 carbon atoms (7–12%), and (c) at least one ester of a saturated long carbon chain acid having 8–18 carbon atoms and an unsaturated short carbon chain acid having 4–12 carbon atoms (10–20%); and copolymers resulting from the polymerization of at least one unsaturated ester and of at least one unsaturated acid.

These compositions present in the form of an aqueous or alcoholic or hydroalcoholic solution can also be provided under pressure, as in a conventional aerosol bomb, admixed with a conventional quantity of a liquefied propellant gas, such as dichlorodifluoromethane, trichlorofluoromethane and their mixtures, to provide an aerosol spray or foam composition for the hair.

In another embodiment of the present invention, the cosmetic compositions can contain, in addition to the cationic polymer and non-toxic salt of a divalent metal, a detergent so as to constitute a shampoo composition.

The detergents usefully employed in these shampoo compositions can be an anionic, non-ionic, cationic or amphoteric detergent.

Representative anionic detergents include: alkyl sulfates, alkylether sulfates, alkyl polyether sulfates, alkyl sulfonates, (the alkyl groups having 8–18 carbon atoms), fatty acid soaps, monosulfosuccinates of fatty alcohols, the condensation product of fatty acids with isethionic acid, the condensation product of fatty acids with methyltaurine, the condensation product of fatty acids with sarcosine and the condensation product of fatty acids with a protein hydrolyzate.

Representative cationic detergents include long chain quaternary ammoniums, esters of fatty acids and amino alcohols, and polyether amines.

Representative non-ionic detergents include esters of polyols and sugars, the condensation product of ethylene oxide with fatty acids, fatty alcohols, long chain alkylphenols, long chain mercaptans or long chain amides, polyethers of polyhydroxy fatty alcohols.

Representative amphoteric detergents include asparagine derivatives, the condensation product of monochloroacetic acid and imidazolines and the alkylamino proprionates.

In these shampoo compositions the concentration of the detergent is generally between about 5 and 50 weight percent and the concentration of the cationic copolymer is between about 3 and 25 weight percent based on the total weight of the composition. The amount of non-toxic salt of a divalent metal in this embodiment is generally that given above.

The concentration of the cationic polymer is, in these shampoo compositions, generally somewhat greater than when the composition is provided in the form of a lotion, inasmuch as after application of the shampoo composition to the hair, the hair is immediately rinsed thereby limiting the contact time of the cationic polymer with the hair.

In another embodiment of the present invention, the compositions can contain, in addition to the cationic polymer and the non-toxic salt of a divalent metal, from about 1 to 10 weight percent of one, and preferably several, natural amino acids or protein hydrolyzates.

Representative natural amino acids that can be employed in this particular embodiment include glycocoll, glutamic acid, aspartic acid, lysine, serine and alanine. These amino acids are natural amino acids that are found combined in the form of polypeptides in substances such as collagen or certain keratinic substances.

By "protein hydrolyzates" is meant the product resulting from the hydrolysis of collagen (or gelatin) or certain keratinic substances such as horn, nails, hair, etc. or other proteinaceous substances such as casein and albumin. In this particular embodiment, the protein hydrolyzates have an average molecular weight less than 10,000 and preferably less than 2,000.

As has been indicated above, these hydrolyzates result from the hydrolysis of collagen for which the principal source is constituted by the skin, bones and certain animal tissues.

The first step of hydrolysis of collagen leads to the formation of gelatin which is a protein of low molecular weight. However, continued hydrolysis of the gelatin, notably with the aid of soda or sulfuric acid, provides the desired protein hydrolyzate. Moreover, it will be noted that the hydrolysis of collagen can, in certain cases, be effected with the aid of certain enzymes.

Thus, the protein hydrolyzates can be produced by the hydrolysis of certain keratinic substances, and when collagen is utilized as an initial reactant, hydrolysis is generally effected with the aid of soda or sulfuric acid. This reaction, when carried out with soda, is usually effected at a temperature lower than that employed when sulfuric acid is used so as to avoid degradation of certain resulting sulfur amino acids, notably methionine and cystine, which are constituents of keratin.

The compositions according to the present invention can also contain any of the usual cosmetic adjuvants such as thickening agents (alkanoamides of fatty acids, carboxymethyl cellulose, hydroxymethyl cellulose, esters of long chain polyols or natural gums), or preservatives such as methyl parahydroxybenzoate or propyl parahydroxybenzoate, dyes and perfumes.

The present invention is also directed to a process for treating hair, particularly degraded hair, to strengthen the mechanical properties of the hair and notably its stability. This process comprises applying to said hair the composition defined above in amounts effective to improve its mechanical stability.

When the composition according to the invention is present in the form of a shampoo, the application is usually followed by rinsing the hair with water and finally drying the hair.

When the composition according to the invention is present in the form of a hair waving lotion, the hair after application of the composition, can be put up on hair waving rollers and dried by application of external heat. After removing the rollers, one obtains according to this hair waving process, excellent waves, the hair being lively, shiny and pleasant to the touch.

The following examples are given to illustrate the present invention.

EXAMPLE 1

A hair waving lotion is prepared in accordance with the present invention by admixing the following components:

| | |
|---|---|
| Polymer resulting from the polycondensation of piperazine and epichlorohydrin (1:1) (MW = 2000) | 2 g |
| Copolymer of vinylpyrrolidone/ vinyl acetate (60:40) K=30-50 (1% solution of ethyl alcohol) | 0.5 g |
| Calcium acetate | 1.2 g |
| Ethyl alcohol | 20 g |
| Perfume | 0.1 g |
| Water, q.s.p. | 100 g |
| pH | 8.7 |

This lotion is applied to degraded hair which previously had been subjected to several bleaching and premanent waving operations.

Initially the hair was washed with a shampoo and then rinsed. Then the preceding lotion was applied to the hair for a period of a few minutes. The thus treated hair was then rolled up on hair waving rollers and dried under a hood at a temperature of about 40°–60°C.

After drying, the rollers were removed and the hair exhibited a good wave, and was more shiny and much more lively than before the said treatment.

This example is repeated except that the quantity of calcium acetate is advantageously replaced by a corresponding molar quantity of iron (FeII) acetate, with comparable results being achieved.

EXAMPLE 2

A gel, in accordance with the present invention, for use in treating degraded hair is prepared by mixing the following components:

| | |
|---|---|
| 50% ethanol solution of GAFQUAT 734, sold by GAF (quaternary copolymer of vinylpyrrolidone, average molecular weight — 100,000) | 5 g |
| Calcium acetate | 1.6 g |
| Cellosize (hydroxyethyl cellulose) | 1.25 g |
| Dye | 0.2 |
| Water, q.s.p. | 100 g |

| | |
|---|---|
| pH | 8 |

After having washed and rinsed the hair which previously had been submitted to several permanent waving and dyeing operations, the preceding gel is applied thereto in amounts to thoroughly impregnate the hair. This treatment imparted to the hair a natural appearance and the thus treated hair was more agreeable to the touch, more shiny and much more lively than before said treatment.

The preceding example was repeated except that the calcium acetate was replaced in one instance by a corresponding molar amount of zinc acetate and in another instance by a corresponding molar amount of cadmium acetate. Essentially the same desirable results, i.e. a general strengthening of the mechanical properties of the hair were achieved in both instances.

EXAMPLE 3

A lotion in accordance with the present invention for treating degraded hair is produced by admixing the following components:

| | |
|---|---|
| 50% ethanol solution of GAFQUAT 734, sold by GAF (quaternary copolymer of vinylpyrrolidone, average MW 100,000) | 2.5 g |
| Protein hydrolyzate (resulting from the total hydrolysis of collagen) | 1 g |
| Calcium gluconate | 3 g |
| Cetyl trimethyl ammonium bromide | 0.1 g |
| Water, q.s.p. | 100 g |
| pH | 7.6 |

After washing bleached hair with a shampoo composition and rinsing the same, the above lotion is applied to the hair for a few minutes. The thus treated hair is subsequently submitted to a hair waving operation and then dried. After this treatment the hair regains its natural appearance, is more shiny, more soft to the touch and much more lively than before said treatment.

The preceding example is repeated except that the calcium gluconate is replaced either by a corresponding molar amount of calcium lactate or calcium pantothenate. Essentially the same desirable results are achieved.

EXAMPLE 4

A hair waving lotion in accordance with the present invention for use in the treatment of degraded hair is prepared by admixing the following components:

| | |
|---|---|
| Polymer resulting from the polycondensation of piperazine and epichlorohydrin (1:2) (MW = 2000) | 0.5 g |
| Glycocoll | 5 g |
| Manganese acetate | 1.8 g |
| Water soluble perfume | 0.1 g |
| Propyl parahydroxybenzoate | 0.3 g |
| Cetylstearyl alcohol oxyethylenated with 15 moles of ethylene oxide per mole of alcohol | 0.3 g |
| Water, q.s.p. | 100 g |
| pH | 6.7 |

This lotion is applied to degraded hair which had previously been submitted to several bleaching operations.

After having washed the hair with a conventional shampoo, and then rinsing the hair, the preceding lotion was applied to the hair for about 5–10 minutes. The hair was then rolled up on hair setting rollers (15–25 mm in diameter) and dried under a hood at a temperature of 35°–45°C.

After drying, the rollers were removed and there was obtained an excellent setting, the hair having a good wave and being soft to the touch. Further, the hair was much less brittle than before said treatment.

EXAMPLE 5

In accordance with the present invention a hair setting lotion for the treatment of hair strongly degraded by previous chemical treatments is prepared by admixing the following components:

| | |
|---|---|
| Quaternary derivatives of cellulose ethers (known under the commercial name of JR-400 sold by Union Carbide | 1 g |
| Glycocoll | 5 g |
| Strontium acetate | 2.5 g |
| Cetyltrimethylammonium chloride | 0.5 g |
| Methyl parahydroxybenzoate | 0.3 g |
| Water soluble perfume | 0.2 g |
| Ethyl alcohol | 10 g |
| Dye | 0.1 g |
| Water, q.s.p. | 100 g |
| pH | 5.9 |

This lotion was applied to the hair under essentially the same conditions as in the preceding example. There was thus obtained an excellent setting, the hair being supple and soft to the touch.

EXAMPLE 6

A gel for use in strengthening degraded hair is prepared by admixing the following components:

| | |
|---|---|
| 50% ethanol solution of GAFQUAT 734 (sold by GAF, quaternary vinylpyrrolidone copolymer, average molecular weight — 100,000) | 5 g |
| Protein hydrolyzate (resulting from the total hydrolysis of collagen) | 5 g |
| Hydroxyethyl cellulose | 2 g |
| Magnesium silicate | 1.6 g |
| Methyl parahydroxybenzoate | 0.5 g |
| Water soluble perfume | 0.2 g |
| Water, q.s.p. | 100 g |
| pH | 7.1 |

After washing and rinsing previously bleached hair, the above gel is applied to the hair in a quantity sufficient to thoroughly impregnate all the hair. The gel is permitted to remain in contact with the hair for about 5–10 minutes. The hair is then rinsed with water, rolled up on curlers and dried.

This treatment imparted to the hair a good appearance, the hair exhibiting all the physical characteristics of natural hair not previously having been submitted to any degrading treatment.

EXAMPLE 7

An emulsion for treating hair weakened by numerous bleachings is prepared by admixing the following components:

| | |
|---|---|
| Cetylstearyl alcohol | 3.3 g |
| Lanolin alcohol oxyethylenated with 20 moles of ethylene oxide per mole of alcohol | 0.7 g |
| 20% aqueous solution of GAFQUAT 755 (sold by GAF, quaternary copolymer of vinylpyrrolidone, average molecular weight greater than 1,000,000) | 1 g |
| Protein hydrolyzate (resulting from | |

| -continued | |
|---|---|
| the total hydrolysis of collagen) | 5 g |
| Wheat germ oil | 1 g |
| Calcium gluconate | 4.5 g |
| Methyl parahydroxybenzoate | 0.3 g |
| Water soluble perfume | 0.2 g |
| Water, q.s.p. | 100 g |
| pH | 5.6 |

This emulsion was applied to the hair under essentially the same conditions set forth in Example 6. The treatment resulted in an excellent strengthening of the hair.

Equally favorable results are also obtained when in the preceding composition calcium gluconate is replaced by a corresponding molar quantity of either magnesium or zinc lactate.

EXAMPLE 8

A shampoo composition for treating degraded hair is prepared by admixing the following components:

| | |
|---|---|
| Triethanolamine lauryl sulfate | 7 g |
| 20% aqueous solution of GAFQUAT 755 (same as in Example 7) | 15 g |
| Protein hydrolyzate (resulting from the total hydrolysis of collagen) | 3 g |
| Calcium acetate | 2 g |
| Water, q.s.p. 100 | g |
| pH | 7 |

This shampoo composition is applied to hair and left in contact therewith for about 5–10 minutes. Thereafter the hair is rinsed with water, rolled upon hair setting curlers and dried. This treatment imparted to the hair all the favorable characteristics noted above.

The above example is repeated except that the calcium acetate is replaced by a corresponding molar amount of calcium nitrate. Equally favorable results are achieved.

EXAMPLE 9

A gel for treating degraded hair is prepared by admixing the following components:

| | |
|---|---|
| Quaternary copolymer resulting from the copolymerization of 43% methyl methacrylate, 14% octadecyl methacrylate and 43% dimethylaminoethyl methacrylate reticulated with the aid of diethylene glycol methacrylate and quaternized with the aid of dimethyl sulfate (MW 1,200,000) | 2.5 g |
| Calcium acetate | 1.6 g |
| Hydroxyethyl cellulose | 1.25 g |
| Dye | 0.2 g |
| Water, q.s.p. | 100 g |
| pH | 6 |

After washing and rinsing hair which had previously been submitted to several permanent waving and dyeing operations, the preceding gel was applied to the hair in amounts sufficient to thoroughly impregnate the hair. This treatment imparted to the hair a natural appearance, the hair being more pleasing to the touch, more shiny and much more lively than before said treatment.

What is claimed is:

1. A homogeneous cosmetic composition for treating degraded hair comprising (a) a cosmetic vehicle selected from the group consisting of water, ethanol, isopropanol and mixtures thereof; (b) 0.2 to 25 percent by weight of at least one cationic polymer having an average molecular weight between about 1,000 and 3,000,000 and being selected from the group consisting of i. a quaternary derivative of cellulose ether of the formula

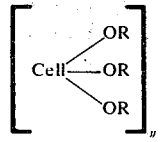

wherein Cell represents the residue of an anhydroglucose unit, $y$ represents a whole number between about 50 and about 20,000 and each R, identical or different, represents a group of the formula

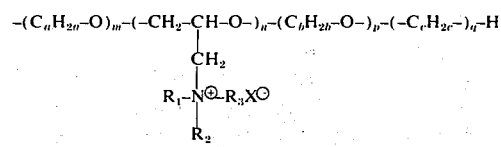

wherein $a$ and $b$ are 2 or 3; $c$ is 1, 2 or 3; $m$ and $p$ are whole numbers from 0–10; $n$ is a whole number from 0–3; $q$ is 0 or 1; $R_1$, $R_2$ and $R_3$ each independently represent a member selected from the group consisting of alkyl, aryl, aralkyl, alkaryl, alkoxyalkyl and alkoxyaryl, said member containing up to 10 carbon atoms and such that the sum of the number of carbon atoms of $R_1$, $R_2$ and $R_3$ ranges from 3–12, with the proviso that when any one or more of $R_1$, $R_2$ and $R_3$ is alkoxyalkyl at least two carbon atoms separate the oxygen of the alkoxy moiety from the nitrogen to which the alkyl moiety is attached; and $X^-$ represents the anion of a mineral or or organic acid;

ii. polymer of the formula

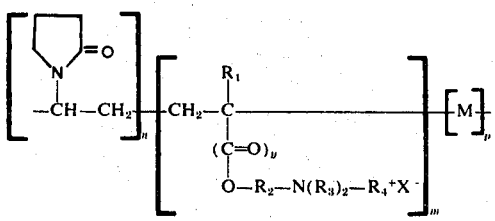

wherein $n$ is a whole number between 20–99, $m$ is a whole number between 1 and 80 and $p$ is a whole number between 0 and 50, with $n+m+p = 100$; $y = 0$ or 1; $R_1$ represents a member selected from the group consisting of hydrogen and methyl; $R_2$ represents a member selected from the group consisting of

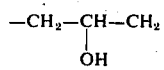

and $C_xH_{2x}$ wherein $x$ is a whole number between 2 and 18; $R_3$ is selected from the group consisting of methyl, ethyl and tert-butyl; $R_4$ is selected from the group consisting of methyl, ethyl and benzyl; $X^\ominus$ represents a member selected from the group consisting of chloride, bromide, iodide, sulfate, bisulfate and $CH_3SO_3$; and M represents a vinyl monomer copolymerizable with N-vinyl pyrrolidone;

iii. a member selected from the group consisting of (1) the polycondensate of piperazine and epichlorohydrin wherein the molar proportion of piperazine to epichlorohydrin ranges from 0.5:2 to 2:0.5, and (2) the quaternary ammonium salt of the polycondensate of (1);

iv. polymer of the formula

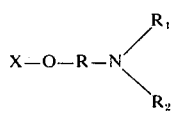

wherein X representz the residue of a starch molecule, R is selected from the group consisting of alkylene and hydroxy alkylene, wherein the alkylene of each contains from 2 to 5 carbon atoms and $R_1$ and $R_2$ are alkyl containing 1 to 5 carbon atoms, phenyl and phenyl alkyl wherein the alkyl moiety contains from 1 to 5 carbon atoms; and v. a member selected from the group consisting of (1') a copolymer of 43–16 weight percent methyl methacrylate, 54–25 weight percent dimethylaminoethyl methacrylate and 12–52 weight percent octadecyl methacrylate, and (2') the quaternary ammonium salt of the copolymer of (1'); and (c) 0.01 – 0.5 mole per gram of said cationic polymer of a non-toxic salt of a divalent metal selected from the group consisting of the carbonate, silicate, nitrate, acetate, gluconate, pantothenate and lactate of calcium, magnesium, manganese, iron, strontium, zinc and cadmium.

2. The composition of claim 1 wherein said cationic polymer is present in amounts of about 0.5–12 percent by weight of said composition.

3. The composition of claim 1 having a pH between about 3–9.

4. The composition of claim 1 which also includes 1–10 weight percent of at least one amino acid or a protein hydrolyzate.

5. The composition of claim 4 wherein the amino acid is selected from the group consisting of glycocoll, glutamic acid, aspartic acid, lysine, serine and alanine.

6. The composition of claim 4 wherein the protein hydrolyzate has an average molecular weight lower than 10,000.

7. The composition of claim 6 wherein the protein hydrolyzate has an average molecular weight lower than 2,000.

8. The composition of claim 1 which also includes under pressure a liquefied propellant gas selected from the group consisting of dichlorodifluoromethane, trichlorofluoromethane and mixtures thereof.

9. A process for treating degraded hair so as to improve its mechanical stability comprising applying to said hair the composition of claim 1 in an amount effective to improve its mechanical stability.

10. The process of claim 9 which includes subsequent to the application of said composition to said hair, rinsing and drying said hair.

11. The process of claim 9 which includes subsequent to the application of said composition to said hair, rolling said hair up on curlers, and drying said hair by the application thereto of external heat.

* * * * *

UNITED STATES PATENT AND TRADEMARK OFFICE
CERTIFICATE OF CORRECTION

PATENT NO. : 3,958,581
DATED : May 25, 1976
INVENTOR(S) : Jean-Louis Abegg et al It is certified that error appears in the above—identified patent and that said Letters Patent is hereby corrected as shown below:

In the Abstract of the Disclosure, in line 4, paragraph (c), "0.01-0.5" should read --about 0.005-0.05--.

In claim 1, paragraph (c), line 1, "0.01-0.5 mole per gram" should read --about 0.005-0.05 mole per gram--.

Signed and Sealed this

Nineteenth Day of August 1980

[SEAL]

*Attest:*

SIDNEY A. DIAMOND

*Attesting Officer*   *Commissioner of Patents and Trademarks*